United States Patent
Uchida (10) Patent No.: US 9,010,934 B2
(45) Date of Patent: Apr. 21, 2015

(54) OPTICAL COHERENCE TOMOGRAPHY APPARATUS, IMAGE PROCESSING APPARATUS, IMAGE PROCESSING METHOD, AND STORAGE MEDIUM OF PROGRAM

(75) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 212 days.

(21) Appl. No.: 13/430,515

(22) Filed: Mar. 26, 2012

(65) Prior Publication Data

US 2012/0249962 A1 Oct. 4, 2012

(30) Foreign Application Priority Data

Mar. 31, 2011 (JP) ................................. 2011-079367

(51) Int. Cl.
*A61B 3/14* (2006.01)
*A61B 3/10* (2006.01)

(52) U.S. Cl.
CPC ...................................... *A61B 3/102* (2013.01)

(58) Field of Classification Search
USPC ......................................... 351/206–221, 246
See application file for complete search history.

(56) References Cited

U.S. PATENT DOCUMENTS

| 2010/0110172 A1* | 5/2010 | Satake ............................. 348/78 |
| 2011/0102742 A1* | 5/2011 | Miyasa et al. ................ 351/206 |
| 2011/0199579 A1* | 8/2011 | Muto ............................ 351/208 |

FOREIGN PATENT DOCUMENTS

| JP | 06-165763 A | 6/1994 |
| JP | 07-255702 A | 10/1995 |
| JP | 09-056707 A | 3/1997 |
| JP | 2003-204939 A | 7/2003 |
| JP | 2008-237238 A | 10/2008 |
| JP | 2010-110392 A | 5/2010 |
| JP | 2011-030911 A | 2/2011 |
| WO | 2009/128213 A | 10/2009 |

* cited by examiner

*Primary Examiner* — Ricky Mack
*Assistant Examiner* — Robert E Tallman
(74) *Attorney, Agent, or Firm* — Canon USA Inc. IP Division (57) ABSTRACT

An optical coherence tomography apparatus includes a generation unit configured, based on interfering light produced by interfering a return beam and a reference beam of light emitted toward the object to be measured, to generate tomographic images of an object to be measured, an image processing unit configured to perform image processing for increasing image quality to at least one of the tomographic images generated by the generation unit, and a display control unit configured to display one of the tomographic images generated by the generation unit and then display the image on which the image processing is performed by the image processing unit on a display unit.

14 Claims, 10 Drawing Sheets

OPTICAL COHERENCE TOMOGRAPHY APPARATUS, IMAGE PROCESSING APPARATUS, IMAGE PROCESSING METHOD, AND STORAGE MEDIUM OF PROGRAM

BACKGROUND OF THE INVENTION

1. Field of the Invention

The present invention relates to an optical coherence tomography apparatus. More particularly, the present invention relates to an optical coherence tomography apparatus for displaying a tomographic image.

2. Description of the Related Art

In recent years, optical coherence tomography apparatuses using a principle of optical coherence tomography (OCT) in which multi-wavelength interference is employed have been increasingly applied to the diagnosis of human bodies. For example, the OCT apparatuses have become to be applied to endoscopes to acquire information about internal organs or to ophthalmologic apparatuses to acquire information about retinas. The optical coherence tomography apparatuses applied for the diagnosis of eyes have become essential as the ophthalmologic apparatuses in outpatient clinics specialized in retina care. The OCT apparatuses irradiate a sample with a measuring beam, which is low coherent light, so that the OCT apparatuses can measure back scattering light from the sample with an interference system. When the OCT apparatuses are applied to the diagnosis of eyes, the apparatus can capture tomographic images of a subject eye at a high resolution by scanning the subject eye with the measuring beam. Using the advantage, the apparatuses are widely used for ophthalmic diagnosis for retinas, and the like.

However, in the OCT apparatus, speckle noise is produced by interference of scattering light due to a structure of a measurement target. Further noise depending on the sensitivity of a detector (a line sensor or a photo diode) may be produced due to reduction of the light amount for reducing a load. To solve the problems, Japanese Patent Application Laid-Open No. 2010-110392 discusses a technique for increasing image quality of tomographic images by scanning the same part of a subject eye a plurality of times, aligning the tomographic images captured by the scanning, and averaging the values.

Further, Japanese Patent Application Laid-Open No. 2008-237238 discusses an optical coherence tomography apparatus for increasing image quality of tomographic images by aligning a plurality of adjacent tomographic images and combining the images. As described above, to obtain high-quality tomographic images in the optical coherence tomography apparatuses, the processing for reducing the noise, for example, by aligning the plurality of acquired tomographic images and combining the images, is important.

However, in the above-mentioned optical coherence tomography apparatuses, the tomographic image is displayed after the alignment and combination of the plurality of tomographic images. As a result, the examiner cannot see the tomographic image until the alignment and combination processing is completed. Consequently, it is difficult to determine whether the image has been successfully captured right after the image capturing.

Meanwhile, when a subject eye is scanned and images of the subject eye are captured, the same part of the subject eye is scanned a plurality of times, and the acquired tomographic images are added to reduce speckle noise, random noise, and the like. In another method, the imaging regions of the subject eye are moved to capture tomographic images. Further in another method, the same part is scanned a plurality of times and the imaging regions of the subject eye are moved to capture tomographic images. However, by the above-mentioned image capturing methods, it is not possible to change the image for checking whether the image capturing has been successfully performed.

SUMMARY OF THE INVENTION

The present invention is directed to an optical coherence tomography apparatus that enables examiners to readily check whether image capturing of a tomographic image has been successfully performed.

According to an aspect of the present invention, an optical coherence tomography apparatus is provided. The optical coherence tomography apparatus includes a generation unit configured, based on interfering light produced by interfering a return beam and a reference beam of light emitted toward the object to be measured to generate tomographic images of an object to be measured, an image processing unit configured to perform image processing for increasing image quality to at least one of the tomographic images generated by the generation unit, and a display control unit configured to display one of the tomographic images generated by the generation unit and then display the image on which the image processing is performed by the image processing unit on a display unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
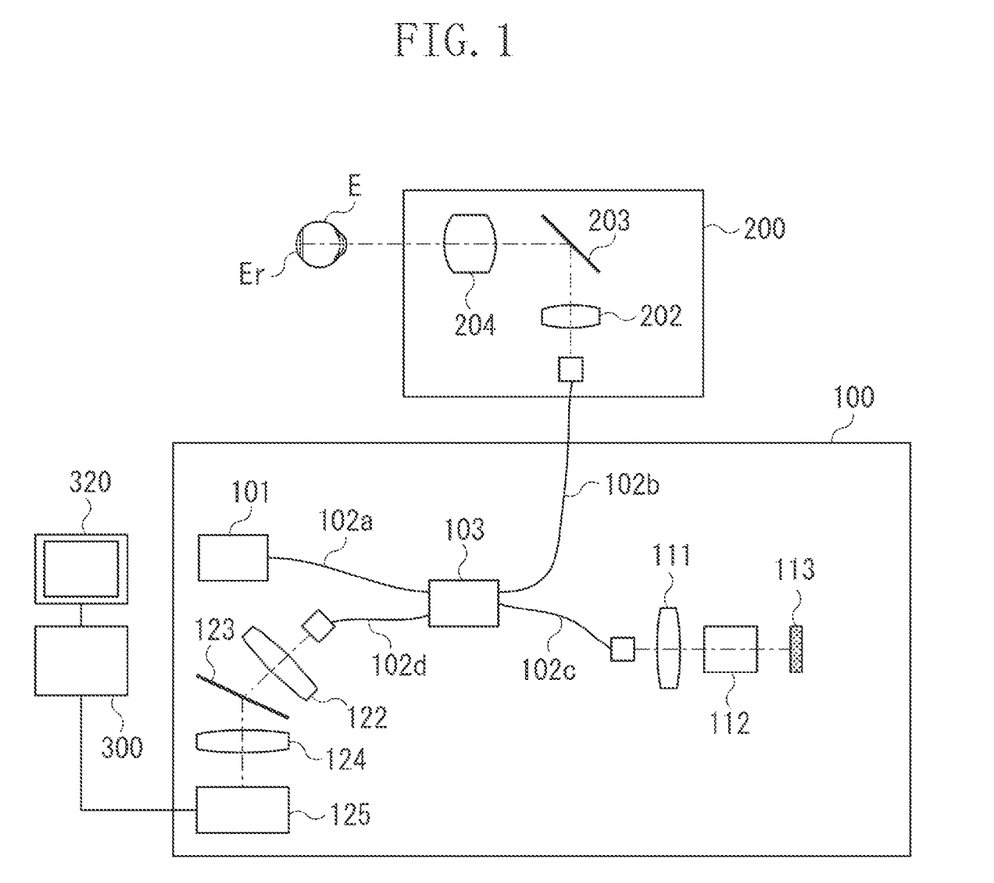
FIG. 1 illustrates an example of an optical coherence tomography apparatus according to an exemplary embodiment of the present invention.

FIG. 1 illustrates an example of an optical coherence tomography apparatus suitable for capturing images of a fundus oculi and a cornea of an eye according to an exemplary embodiment of the present invention. In the exemplary embodiment, particularly, an optical coherence tomography apparatus suitable for capturing fundus oculi images is described.

An optical interference unit 100 includes a light source 101. The light source 101 is a low-coherence source that emits near infrared light. The light emitted from the light source 101 travels through an optical fiber 102a, and is split into a measuring beam and a reference beam by a light splitting unit 103. The measuring beam split by the light splitting unit 103 enters an optical fiber 102b, and is guided to a scanning optical system 200. The reference beam split by the light splitting unit 103 enters an optical fiber 102c, and is guided to a reflection mirror 113.

The reference beam entered the optical fiber 102c exits from the fiber end. Then, the reference beam enters a dispersion compensation optical system 112 via a collimating optical system 111, and is guided to the reflection mirror 113. The reference beam reflected by the reflection mirror 113 travels through the reverse optical path and enters the optical fiber 102c again. The dispersion compensation optical system 112 is used to correct dispersion in the optical system in the scanning optical system 200 and a subject eye E that is a subject to be measured. The reflection mirror 113 is configured to be capable of being driven in an optical axis direction by an optical path length control unit 114 (not illustrated). The reflection mirror 113 can change optical path lengths of the reference beam relative to optical path lengths of the measuring beam. The measuring beam entered the optical fiber 102b exits from the fiber end. The light source 101 and the optical path length control unit 114 are controlled by a control unit 130 (not illustrated).

Next, the scanning optical system 200 is described. The scanning optical system 200 is an optical system that is configured to be capable of moving relative to the subject eye E. A drive control unit 205 (not illustrated) in the scanning optical system is configured to be capable of driving the scanning optical system 200 in the vertical and horizontal directions with respect to the eye axis of the subject eye E. In a case of an endoscope, for example, the endoscope is configured to be provided with the scanning optical system 200 at a tip portion of a fiberscope.

The light emitted from the fiber end of the optical fiber 102b is made to be substantially parallel by an optical system 202, and enters a scanning unit 203. The scanning unit 203 includes two galvanometer mirrors that can rotate their mirror surfaces. One of the galvanometer mirrors deflects the light in the horizontal direction, and the other galvanometer mirror deflects the light to the vertical direction. The galvanometer mirrors deflect the incident light by control of the drive control unit 205. By the operation, the scanning unit 203 can perform scanning in two directions; in the main scanning direction in the drawing and in the sub-scanning direction that is the vertical direction in the drawing. The light emitted from the scanning unit 203 forms an illumination spot on a retina Er of the subject eye E via a lens 204. When the scanning unit 203 performs in-plane deflection, each illumination spot moves on the retina Er. The reflected light at the illumination spot point travels through the reverse optical path, enters the optical fiber 102b, and returns to the light splitting unit 103.

As described above, the reference beam reflected by the reflection mirror 113 and the measuring beam reflected from the subject eye retina Er return to the light splitting unit 103 as the returned light, and causes optical interference. The light interfered with each other passes through an optical fiber 102d. The interfering light emitted to a lens 122 is made to be substantially parallel, and enters a diffraction grating 123. The diffraction grating 123 has a periodic structure such that the input interfering light is dispersed. The dispersed interfering light forms and image on a line sensor 125 with an imaging lens 124. The imaging lens 124 can change in-focus states. The line sensor 125 is connected to an image processing device 300.

Figure 2:
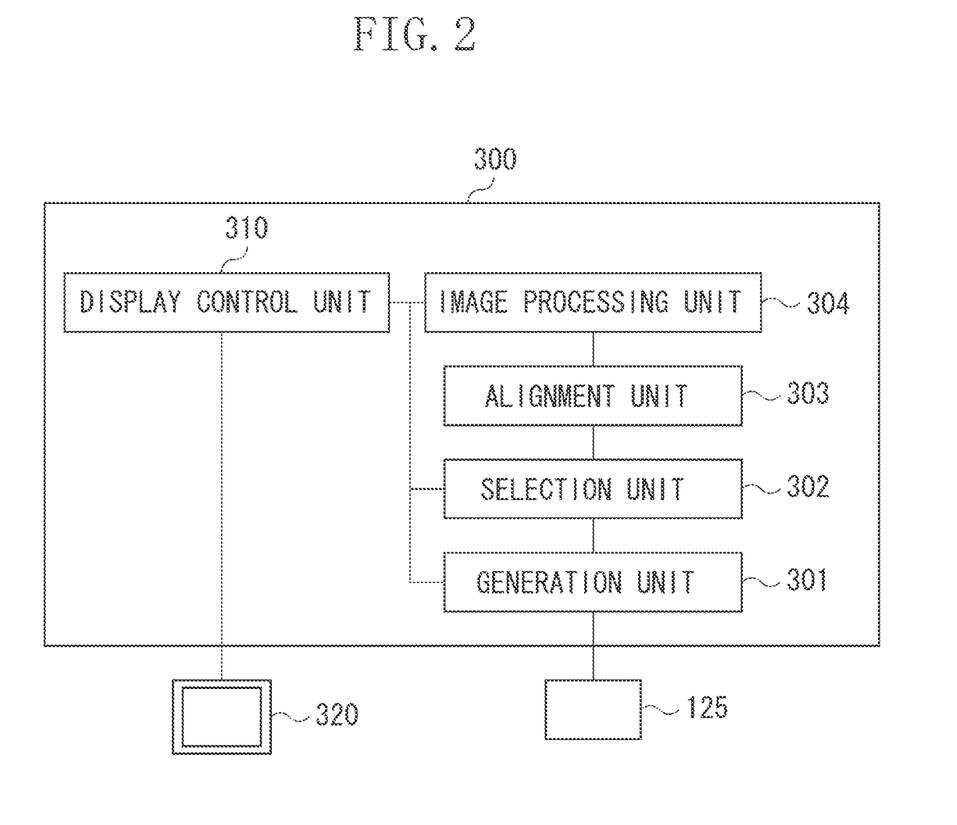
FIG. 2 illustrates an example of an image processing apparatus.

FIG. 2 illustrates the image processing device 300. As illustrated in FIG. 2, the image processing device 300 includes a generation unit 301. In the exemplary embodiment, the optical coherence tomography apparatus employs a Fourier domain technology. The OCT apparatus generates a tomographic image of a retina by performing Fourier transform on data output from the line sensor 125 with the generation unit 301. The generation unit 301 is configured to be connected to a display control unit 310 such that the generated tomographic image can be displayed.

The image processing device 300 includes a selection unit 302 that evaluates image quality of the generated tomographic image to select the tomographic image. Using a luminance value of the tomographic image generated in the generation unit 301, the selection unit 302 can calculate an evaluation value of the image quality of the tomographic image. Further, the selection unit 302 determines a reference tomographic image using the calculated evaluation value, and is configured to be capable of displaying the reference tomographic image on a monitor 320 via the display control unit 310.

An alignment unit 303 can detect a positional relationship between the reference tomographic image and arbitrary tomographic image, and output the aligned tomographic images to an image processing unit 304. The image processing unit 304 performs processing for reducing a noise of the tomographic image generated in the generation unit 301. Alternatively, the image processing unit 304 can perform processing for increasing a contrast. In an example in the exemplary embodiment, a plurality of tomographic images is averaged such that a tomographic image having increased image quality is to be generated. In the exemplary embodiment, the increase of the image quality means to reduce the noise of the image, or to increase a signal-to-noise (S/N) ratio by increasing the contrast of the image. The image processing unit 304 is connected to the display control unit 310 and is configured to be capable of displaying the combined tomographic image on the monitor 320. The image processing unit 304 can perform processings other than the above-mentioned processings to reduce the noise or increase the contrast to the tomographic image. For example, the image processing unit 304 can perform a sharpening processing for amplifying amplitude of a high-frequency component of the tomographic image or a noise reduction processing for removing an isolated shadow.

The display control unit 310 is connected to the monitor 320. The display control unit 310 can display a tomographic image input from the processing unit. As described above, the optical coherence tomography apparatus includes the optical interference unit 100, the scanning optical system 200, and the image processing device 300. The components are controlled by the control unit 130. The control unit 130 includes a central processing unit (CPU) 140 (not illustrated). The control unit 130 executes operation by loading a control program 150 into a random access memory (RAM) 160 (not illustrated). It is also possible to provide a control unit having a CPU, a graphics processing unit (GPU), or the like for each of the optical interference unit 100, the scanning optical system 200, and the image processing device 300, and control the components using individual programs.

At least a part of the individual units in the image processing device 300 may be implemented as an independent device. Alternatively, each unit may be implemented as software implementing the function by installing the software in one or a plurality of computers and executing the software by a CPU 330 (not illustrated) of the computer. In the exemplary embodiment, each individual unit is implemented by the software, and the software is installed in the same computer.

The CPU 330 performs overall control of the computer using a program or data stored in a RAM 3302 (not illustrated) or a read-only memory (ROM) 3303 (not illustrated). Further, the CPU 330 controls the execution of the software in each individual unit to implement the functions of each individual unit. The RAM 3302 includes an area for temporarily storing a program or data loaded from a storage medium drive 3308 and a work area necessary for the CPU 330 for performing various kinds of processing. Generally, the ROM 3303 stores a computer program and setting data.

The image processing device 300 can be configured as an electric circuit using an image processing board. A control method in the control unit 130 for capturing a plurality of tomographic images of a subject eye fundus oculi in the OCT apparatus is described.

First, the examiner has a patient sit in front of the optical coherence tomography apparatus according to the exemplary embodiment. Then, the examiner starts the OCT imaging. The light emitted from the light source 101 passes through the optical fiber 102a. The light is split into the measuring beam that travels toward the subject eye and the reference beam that travels toward the reflection mirror 113 in the light splitting unit 103. The measuring beam traveling toward the subject eye passes through the optical fiber 102b and exits from the fiber end. The light is made to be substantially parallel by the optical system 202, and enters the scanning unit 203. The scanning unit 203 includes the galvanometer mirrors. The measuring beam that is deflected by the mirrors travels via the optical system 204 and emitted toward the subject eye fundus oculi. The light reflected by the subject eye travels the reverse path and returns to the light splitting unit 103.

Meanwhile, the reference beam that travels toward the reflection mirror passes through the optical fiber 102c and exits from the fiber end. The light passes through the collimating optical system 111 and the dispersion compensation optical system 112 and reaches the reflection mirror 113. The reference beam reflected by the reflection mirror 113 travels the reverse path and returns to the light splitting unit 103.

The measuring beam and the reference beam returned to the light splitting unit 103 interfere with each other, and become interfering light. The interfering light enters the optical fiber 102d and is made to be substantially parallel by an optical system 122. The light enters the diffraction grating 123. The interfering light input into the diffraction grating 123 forms an image on the line sensor 125 by the imaging lens 124, thereby an interference signal at a point on the subject eye fundus oculi can be obtained. The interference signal acquired by the line sensor 125 is output to the image processing device 300. In the generation unit 301, frequency conversion and fast Fourier transformation (FFT) processing is performed such that the data is visualized as a tomographic image in the depth direction at the point on the subject eye fundus oculi. After the acquisition of the tomographic image at the point on the subject eye fundus oculi, the scanning unit 203 drives the galvanometer mirrors, and generates interfering light at a different point on the subject eye fundus oculi. The interfering light at the different point passes through the line sensor 125, and forms a tomographic image in the depth direction at the different point on the subject eye fundus oculi. The continuous drive of the galvanometer mirrors by the scanning unit 203 enables generation of a sheet of tomographic image of the subject eye fundus oculi.

In the exemplary embodiment, a first mode, a second mode, and a third mode are provided. In the first mode, one point of the subject eye is scanned a plurality of times to acquire tomographic images at the same point. In the second mode, scanning points of the subject eye are moved to capture tomographic images at a plurality of points. In the third mode, one point is scanned a plurality of times and scanning points of the subject eye are moved to capture tomographic images at the plurality of points. Since eyes slightly move or shift, it is not possible to precisely capture images at a the same point. Consequently, scanning the same point a plurality of times means scanning a plurality of times with the same scanning trajectory as that of the galvanometer mirrors.

Hereinafter, an example in the first mode is described.

After the scanning unit 203 generates a sheet of subject eye tomographic image, the scanning unit 203 generates a plurality of tomographic images in the same scanning trajectory. For the purpose, the scanning unit 203 repeats scanning at substantially the same point on the fundus oculi. By the plurality of scanning operations, the generation unit 301 can generate a plurality of sheets of tomographic images at substantially the same point on the subject eye fundus oculi.

Figure 3:
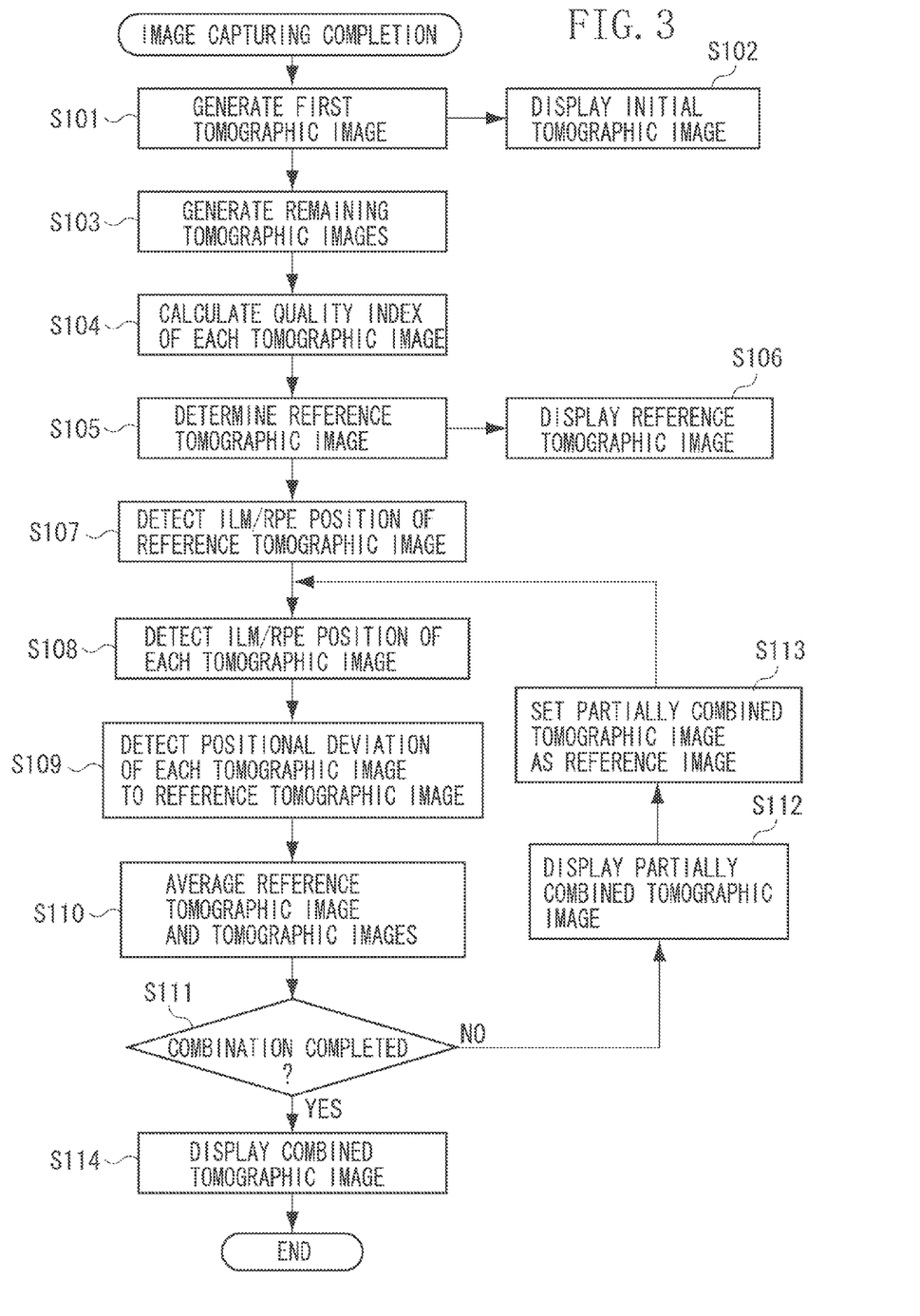
FIG. 3 is a flowchart illustrating an example of operation of displaying a tomographic image.

With reference to FIG. 3, a procedure for displaying a tomographic image that is not completely combined before the completion of alignment of a plurality of tomographic images and the combination processing in the OCT apparatus according to the exemplary embodiment is described.

In step S101, the generation unit 301 generates a first tomographic image of the subject eye fundus oculi and outputs the generated tomographic image to the display control unit 310. In step S102, the display control unit 310 displays the input tomographic image on the monitor 320.

Figure 4:
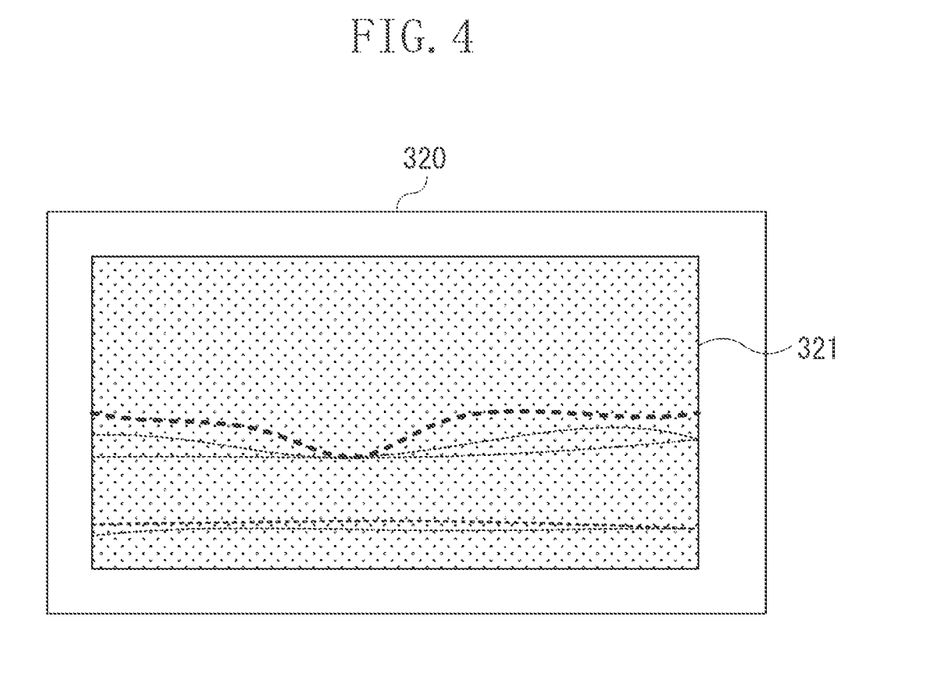
FIG. 4 illustrates an example of display of an initial tomographic image.

As illustrated in FIG. 4, a first tomographic image 321 displayed on the monitor 320 has many noises and often the contrast is unclear. However, sometimes the first tomographic image 321 has a quality adequate for checking the imaging region and the positional relationship of the retina on the image. Accordingly, at the time the first tomographic image 321 is displayed in step S102, the examiner can determine to some extent whether the image capturing has been successfully performed.

Further, scanning with the galvanometer mirrors is performed a plurality of times in the same trajectory to obtain interfering light for acquiring a plurality of sheets of tomographic images at the substantially same portion on the subject eye fundus oculi. In step S103, the generation unit 301 generates the plurality of sheets of tomographic images at the substantially same portion on the subject eye fundus oculi. The plurality of subject eye tomographic images generated by the generation unit 301 are output to the selection unit 302 to determine a reference image that is necessary for alignment.

In step S104, the selection unit 302 calculates an evaluation value for evaluating the image quality of each tomographic image with respect to the all input tomographic images using the luminance value of each pixel in the tomographic images. The method for calculating the evaluation value includes a method of calculating an evaluation value by classifying (calculation of a histogram) all pixels forming a tomographic image into each luminance value and counting the number of pixels having a luminance value within a predetermined range. The method uses a property that the luminance of layers that form a retina is concentrated within a certain range of luminance on a tomographic image. According to the method, the image quality of a tomographic image can be evaluated by the degree of the calculated index.

In the description above, the example of the method of calculating the evaluation value based on the luminance range of the tomographic image is described. However, the evaluation value can be calculated using other methods. For example, a contrast ratio can be calculated based on a luminance value of a tomographic image and the calculated value can be used as a quality index. Further, a S/N ratio can be calculated based on a luminance value of a tomographic image and the calculated value can be used as an evaluation value.

In step S105, the selection unit 302 calculates the evaluation value of each tomographic image. Then, the selection unit 302 specifies a tomographic image that has a highest image quality in the tomographic images, and selects the tomographic image as a reference tomographic image for alignment. The selection unit 302 outputs the selected reference tomographic image to the display control unit 310. In step S106, the display control unit 310 displays the input tomographic image on the monitor 320.

Figure 5:
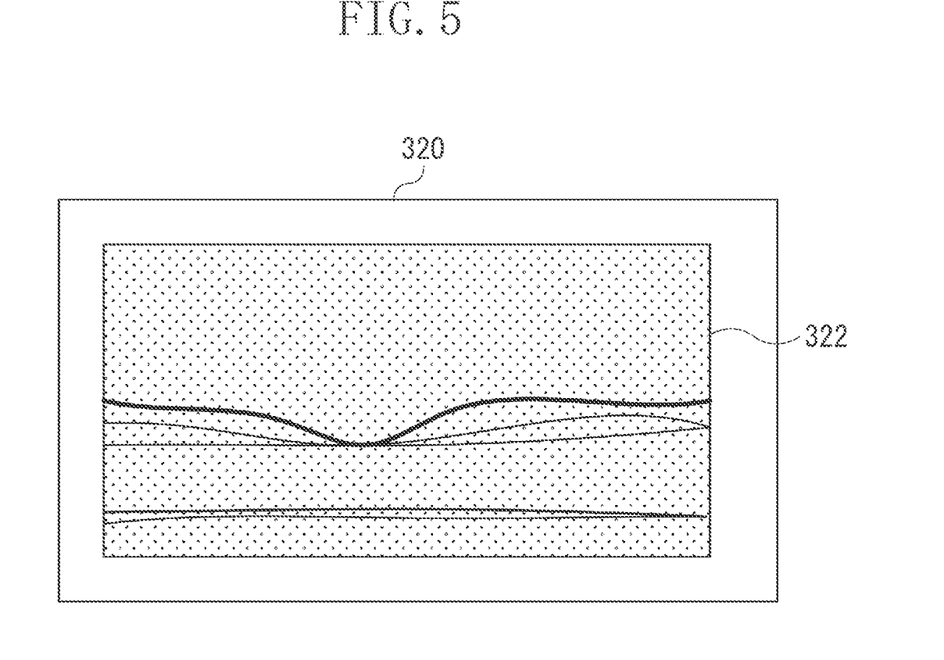
FIG. 5 illustrates an example of display of a reference tomographic image.

As illustrated in FIG. 5, the noise amount of a reference tomographic image 322 displayed on the monitor 320 is similar to that of the first tomographic image 321. However, the contrast is clearer than that of the first tomographic image 321. When the examiner determines whether the image capturing has been successfully performed, the reference tomographic image 322 is more appropriate than the first tomographic image 321. However, the time necessary for displaying a final combined tomographic image is delayed by the time necessary for the display processing of the reference tomographic image 322. To solve the problem, the display control unit 310 can omit the display (step S106) of the reference tomographic image 322.

In the first mode, the tomographic image of the same portion is always displayed. Accordingly, it is advantageous to display the first tomographic image 321 first and then display the reference tomographic image 322. Meanwhile, in the third mode, many tomographic images at different scanning points are displayed and displaying the reference tomographic image 322 may interfere with the checking operation. To solve the problem, in the third mode, it is advantageous to omit to display the reference tomographic image 322.

The examiner can select a mode in which the tomographic image 321 captured first is displayed and then the reference tomographic image 322 is displayed or a mode in which the first tomographic image 321 captured first is displayed and the reference tomographic image 322 is not displayed.

Finally, the selection unit 302 outputs the selected reference tomographic image 322 and all tomographic images other than the reference tomographic image to an alignment unit 303.

The alignment unit 303 executes processing for detecting the positions and shapes of the retina layers on each reference tomographic image 322 to acquire a positional relationship between the input reference tomographic image 322 and the other tomographic images. In step S107, with respect to the reference tomographic image 322, the alignment unit 303 detects the shape and position of an inner limiting membrane (ILM) and a retinal pigment epithelium (RPE) on the tomographic image respectively.

Figure 8:
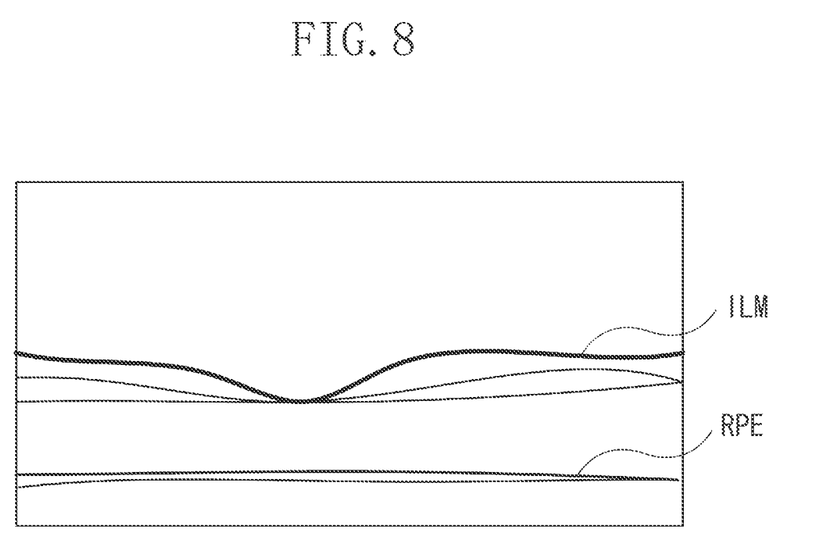
FIG. 8 illustrates retinal layers.

As illustrated in FIG. 8, the ILM is the boundary of the vitreous body and the retina, and the ILM is the uppermost part of the retina. Generally, an optical reflectivity of the retina is higher than that of the vitreous body. Therefore, in the optical coherence tomography apparatus, an optical interference signal intensity of the retina is higher than that of the vitreous body. Consequently, the luminance of the tomographic image captured by the optical coherence tomography apparatus largely changes in the ILM which is the boundary of the vitreous body and the retina. The alignment unit 303 can specify the shape and the position of the ILM by detecting the change of the luminance information.

Meanwhile, as illustrated in FIG. 8, the RPE is a layer of epithelial cells and the RPE is in the boundary of the retina and the choroid coat of an eye. It is known that the RPE is a layer that indicates a highest luminance value in a tomographic image captured by the optical coherence tomography apparatuses. The alignment unit 303 can detect the shape and position of the RPE using the high luminance image information similarly to the ILM.

In step S108, with respect to the tomographic images other than the input reference tomographic image 322, the alignment unit 303 detects the shape and position of each ILM and RPE respectively similarly to the reference tomographic image 322.

Figure 9:
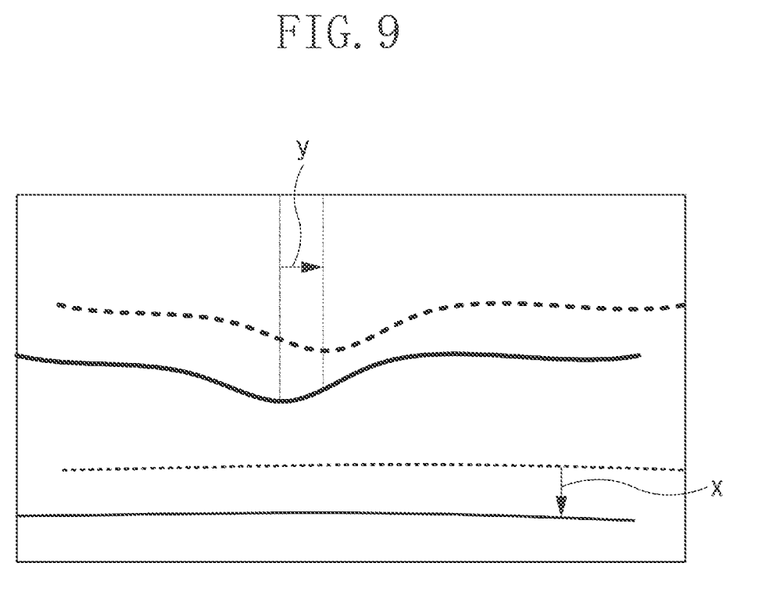
FIG. 9 illustrates a comparison between tomographic images in the vertical and horizontal directions.
Figure 10:
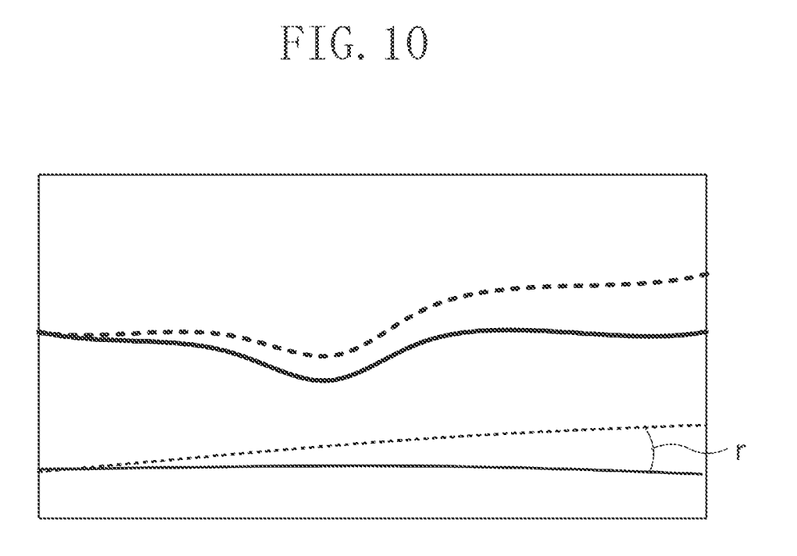
FIG. 10 illustrates a comparison between tomographic images in the rotational direction.

In step S109, the alignment unit 303 calculates positional relationships (amounts of positional deviation) of the tomographic images in which the shapes and positions of the ILM and the RPE layer are detected with respect to the reference tomographic image 322. For example, as illustrated in FIG. 9, by comparing the shapes and positions of the ILM and RPE of the reference tomographic image 322 with those of the target tomographic image, degrees of deviation (x and y) of the target tomographic image with respect to the reference tomographic image 322 in the vertical and horizontal directions can be calculated. Further, for example, as illustrated in FIG. 10, by comparing the inclinations of the ILM and RPE of the reference tomographic image 322 with those of the target tomographic image, a degree of deviation (r) of the target tomographic image with respect to the reference tomographic image 322 in the rotational direction can be calculated.

Using the positional deviation amounts in the vertical and horizontal directions and the positional deviation amount in the rotational direction, each tomographic image is aligned and output to the image processing unit 304.

In the exemplary embodiment, the positional deviation amounts among the tomographic images are calculated by detecting the shapes and positions of the ILMs and the RPEs. However, retina layers or layer boundaries other than the ILM and RPM can be detected and using the shapes and positions of the layers or boundaries, positional deviation amounts between tomographic images can be calculated. Further, not by comparing the shapes and positions of the retinas, but by comparing the luminance values of the tomographic images, the positional deviation amounts can be calculated. For example, by calculating differences between the luminance values of the tomographic images and finding a position where the difference has a smallest value, the positional deviation amount between the tomographic images can be calculated.

In step S110, the image processing unit 304 performs averaging processing on the plurality of aligned tomographic images. The averaging processing is a common averaging processing in which the luminance values of the tomographic images are added, the addition result is divided by the number of tomographic images used for the addition, and the result is to be the luminance value of the new tomographic image. In the exemplary embodiment, using the averaging processing, the combining processing of the tomographic images is implemented. However, the combining processing of the tomographic images can be implemented using other methods. For example, using a median filter, a plurality of tomographic images can be combined.

By the above-described processing from step S108 to S110, the combining processing of the reference tomographic image 322 and a sheet of tomographic image is completed. In step S111, the image processing unit 304 determines whether a tomographic image that has not combined exists.

Figure 6:
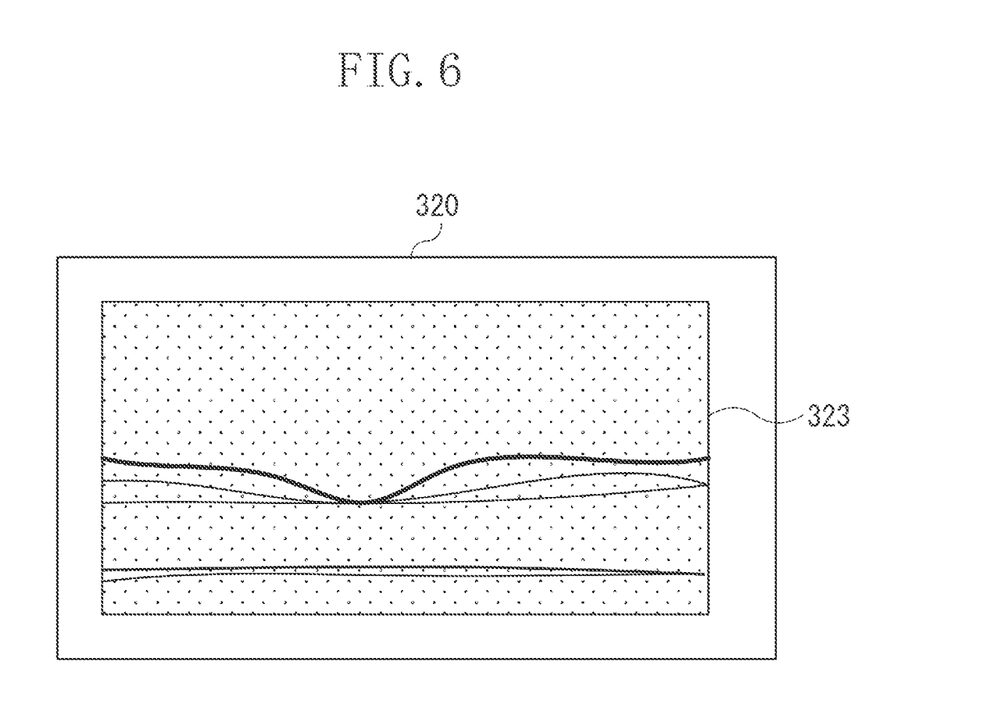
FIG. 6 illustrates an example of display of a partially combined tomographic image.

If a tomographic image that has not combined remains (NO in step S111), in step S112, the image processing unit 304 outputs the combined tomographic image (partially combined tomographic image) at the time to the display control unit 310, and the display control unit 310 displays the input partially combined tomographic image on the monitor 320. As illustrated in FIG. 6, the amount of noise of a partially combined tomographic image 323 displayed on the monitor 320 is smaller than those of the first tomographic image 321 and the reference tomographic image 322, and the contrast is also clear.

When the examiner determines whether the image capturing has been successfully performed, the partially combined tomographic image 323 is more appropriate than the first tomographic image 321 and the reference tomographic image 322. However, the time necessary for displaying a final combined tomographic image may be delayed by the time necessary for the display processing of the partially combined tomographic image 323. To solve the problem, the display control unit 310 can omit the display (step S112) of the partially combined tomographic image 323.

In the first mode, the partially combined tomographic image 323 is displayed. In the third mode, the scanning points are changed and displaying many images may interfere with the checking operation. Accordingly, only a fully combined tomographic image is to be displayed.

The examiner can select a mode in which the partially combined tomographic image 323 is displayed or a mode in which only the fully combined tomographic image is displayed.

In step S113, after the display of the partially combined tomographic image 323 is finished, the image processing unit 304 sets the partially combined tomographic image 323 to the reference tomographic image 322 to perform combination processing of a next tomographic image, and repeats a series of the processings from step S108 to step S111. The repetition of the processings enables sequential display of the latest partially combined tomographic image 323 on the monitor 320.

Figure 7:
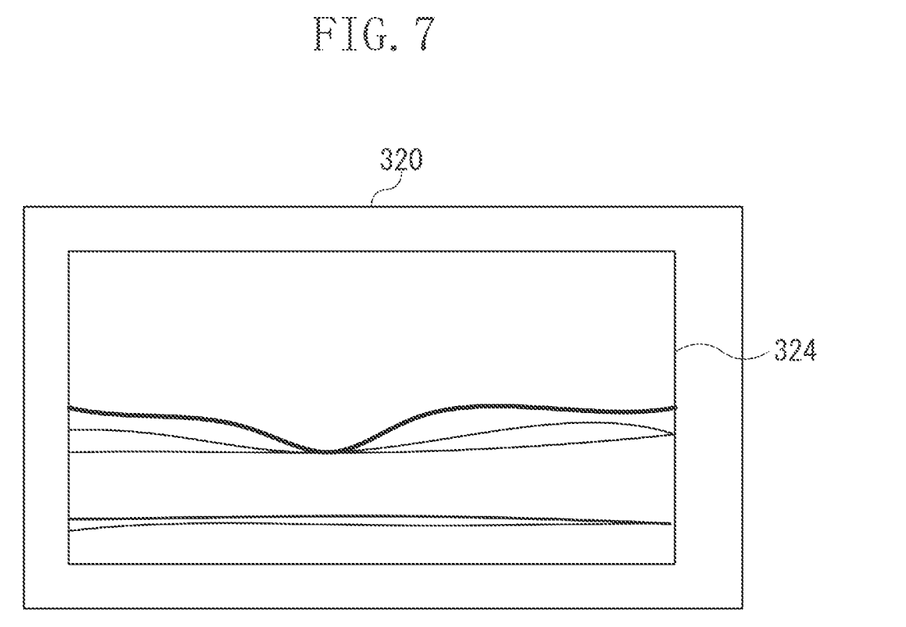
FIG. 7 illustrates an example of display of a combined tomographic image.

After completion of the combining processing of the all tomographic images (YES in step S111), the image processing unit 304 outputs the combined tomographic image to the display control unit 310. In step S114, the display control unit 310 displays an input combined tomographic image 324 on the monitor 320 as illustrated in FIG. 7.

In the exemplary embodiment, the example of sequentially displaying the images on the monitor 320 is described. However, a plurality of images can be displayed on the monitor 320. Further, another monitor may be provided, and different images may be displayed on the individual monitors. In the case the plurality of images is displayed, comparison of the images becomes easy.

In the second mode, when the tomographic images generated in the generation unit 301 are combined, the image processing unit 304 performs adding processing on tomographic images that are captured in temporally sequenced order. The reference tomographic image in such a case is the target tomographic image on which the adding processing is to be performed. The tomographic images generated in the generation unit 301, the tomographic images are displayed on the monitor 320 via the display control unit 310 are displayed in the order the images are captured. The tomographic image on which the image processing is performed in the image processing unit 304 is displayed on the monitor 320 alternately with the tomographic image generated in the generation unit 301.

Further, in the second and third modes, a tomographic image captured first and a tomographic image captured last can be selected using the selection unit 302, and the tomographic images selected using the selection unit 302 can be also displayed on the monitor 320. Since eyes are curved, by displaying the tomographic image captured first and the tomographic image captured last, the determination of success of the image capturing becomes easy.

As described above, the optical coherence tomography apparatus according to the exemplary embodiment can display the tomographic image that enables the examiner to determine whether the image capturing has been successfully performed during the image processing of the tomographic images. Accordingly, immediately after the image capturing, the examiner can determine whether the image capturing has been successfully performed. Further, the examiner can determine whether the image capturing is successfully performed using the image whose image quality is increased as time passes.

The exemplary embodiment has been described in detail above. The present invention can be implemented, for example, as a system, an apparatus, a method, a program, or a storage medium storing the program. Specifically, the present invention can be applied to a system including a plurality of devices or an apparatus consists of a single device.

The present invention can also be achieved by directly or remotely providing a program of software to the system or the device and by reading and executing the provided program code with a computer of the system or the device to achieve the functions of the above-described exemplary embodiment.

Accordingly, the program code itself that is installed on the computer to implement the functional processing according to the exemplary embodiment constitutes the present invention. In other words, the present invention includes the computer program itself that implements the functional processing according to the exemplary embodiment of the present invention.

In such a case, if the function of the program is implemented, any form may be employed, for example, an object code, a program implemented by an interpreter, or script data to be supplied to an operating system (OS).

The computer-readable storage medium for supplying the computer program includes, as the storage medium for supplying the program, for example, a floppy disk, a hard disk, an optical disk, a magneto-optical disk (MO), a compact disk read-only memory (CD-ROM), a compact disk recordable (CD-R), a compact disk rewritable (CD-RW), a magnetic tape, a nonvolatile memory card, a ROM, and a digital versatile disk (DVD) (DVD-ROM, DVD-R) may be employed.

The program may be supplied by connecting to an Internet website using a browser in a client computer. Then, the computer program according to the exemplary embodiment of the present invention may be supplied from the Internet website by downloading the computer program itself into a recording medium such as a hard disk. In such a case, the program to be downloaded may be a compressed file including an automatic installation function. Further, the program code constituting the program according to the exemplary embodiment of the present invention may be divided into a plurality of files, and each file may be downloaded from different Internet websites. In other words, a WWW server that allows downloading of the program file to a plurality of users for implementing the functional processing according to the exemplary embodiment of the present invention in the computer, is also included in the present invention.

Further, the program according to the exemplary embodiment of the present invention may be encrypted and stored on a storage medium such as a CD-ROM, and distributed to the users. In such a case, a user who has cleared prescribed conditions is allowed to download key information for decrypting from a home page through the Internet. Using the key information, the user is allowed to execute the encrypted program, and the program is installed into the computer.

In addition to the implementation of the functions of the above-described exemplary embodiment by executing the read program by the computer, according to an instruction of the program, the functions according to the exemplary embodiment can be implemented in cooperation with an OS running on the computer, or the like. In such a case, the OS or the like can carry out apart of or the whole of the actual processing, thereby implementing the above-described functions of the above-described exemplary embodiment.

Further, the program code read from the storage medium may be written in a memory which is provided in a function enhancing board inserted in the computer or in a function enhancing unit connected to the computer, and a part of or all of the functions according to the above-described exemplary embodiment may be implemented. In such a case, after the program is written in the function expansion board or the function expansion unit, according to the instructions of the program, the CPU provided in the function expansion board or the function expansion unit or the like wholly or partially executes actual processing.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-079367 filed Mar. 31, 2011, which is hereby incorporated by reference herein in its entirety.

What is claimed is:

1. An optical coherence tomography apparatus comprising:
   a generation unit configured, based on interfering light produced by interfering return light of light emitting toward an object to be measured and reference light, to generate tomographic images of the substantially same scanning line portion on the object to be measured;
   an image processing unit configured to generate a combined image by averaging a plurality of the tomographic images generated by the generation unit; and
   a display control unit configured to display one image of the plurality of the tomographic images while the image processing unit is generating the combined image and then change from display of the one image of the plurality of tomographic images to display of the combined image on a display unit.

2. The optical coherence tomography apparatus according to claim 1, further comprising:
   a scanning optical system configured to scan the object to be measured with light; and
   a selection unit configured to select the one image from the plurality of tomographic images,
   wherein, the selection unit selects the one image depending on selection of a first mode for acquiring a plurality of tomographic images by scanning the object a plurality of times through the scanning optical system in the same trajectory, or a second mode for capturing tomographic images at a plurality of points by changing the scanning points of the object through the scanning optical system.

3. The optical coherence tomography apparatus according to claim 1, further comprising:
   an evaluation unit configured to evaluate each of the plurality of tomographic images,
   wherein the selection unit selects a tomographic image from the plurality of tomographic images based on evaluation values by evaluation unit, and
   wherein the tomographic image displayed on the display unit is the tomographic image selected by the selection unit.

4. The optical coherence tomography apparatus according to claim 3, wherein the image processing unit combines the plurality of tomographic images using the tomographic image selected by the selection unit as a reference for alignment.

5. The image processing apparatus according to claim 1, wherein the display control unit displays the tomographic image generated by the generation unit until the combining is completed.

6. The image processing apparatus according to claim 3, wherein the evaluation values are values for evaluating the image quality of each of the tomographic images, and
   wherein the tomographic image selected by the selection unit is a tomographic image having a finest image quality in the tomographic images generated by the generation unit.

7. The image processing apparatus according to claim 6, wherein the evaluation value is calculated based on a luminance value of the tomographic image.

8. The optical coherence tomography apparatus according to claim 1, further comprising:
   a scanning optical system configured to scan the object to be measured with the light,
   wherein, the tomographic image displayed on the display unit is a tomographic image obtained first by scanning the object to be measured by the scanning optical system.

9. The image processing apparatus according to claim 1, wherein the image processing unit sequentially combines the plurality of tomographic images, and
   wherein the display control unit sequentially displays the combined image.

10. The optical coherence tomography apparatus according to claim 4, further comprising:
    an extraction unit configured to extract inner limiting membranes and/or retinal pigment epitheliums in the tomographic images; and
    an alignment unit configured, based on the inner limiting membranes and/or the retinal pigment epitheliums extracted by the extraction unit, to align the reference tomographic image and the other tomographic images,
    wherein the image processing unit combines the tomographic images aligned by the alignment unit.

11. An optical coherence tomography apparatus comprising:
    a light source;
    an optical system configured to split light emitted from the light source into measuring light with which a fundus oculi of a subject eye is irradiated through a scanning optical system and reference light, and obtain interfering light generated by interfering return light from the fundus oculi of the subject eye and the reference light;

a sensor configured to convert the interference light to an interference signal;

a generation unit configured to generate a plurality of tomographic images of the substantially same scanning line portion on the subject eye based on the interference signal;

an image processing unit configured to generate a combined image by averaging the plurality of tomographic images generated by the generation unit; and a monitor configured to display one of the tomographic images while the image processing unit is generating the combined image and then change from display of the one image of the plurality of the tomographic images to display of the combined image.

12. An image processing apparatus for performing image processing on a tomographic image of an object to be measured, the image processing apparatus comprising:

an image processing unit configured to generate a combined image by averaging a plurality of tomographic images of the object to be measured, the plurality of tomographic images including tomographic images generated of the substantially same scanning line portion; and a display control unit configured to display one of the plurality of tomographic images while the image processing unit is generating the combined image and then change from display of the one image of the plurality of the tomographic images to display of the combined image on the display unit.

13. An image processing method for performing image processing on a tomographic image of an object to be measured, the image processing method comprising:

acquiring a plurality of tomographic images of the substantially same scanning line portion on the object to be measured;

generating a combined image by averaging the plurality of the tomographic images; and displaying one of the acquired tomographic images while the combined image is generating in the generating step and then changing from displaying of the one image of the plurality of the tomographic images to displaying of the combined images.

14. A computer-readable storage medium storing a program for causing a computer to function as units comprising:

a generation unit configured, based on interfering light produced by interfering return light of light emitted toward an object to be measured and reference light, to generate tomographic images of the substantially same scanning line portion on an object to be measured;

an image processing unit configured to generate a combined image by averaging the plurality of the tomographic images generated by the generation unit; and a display control unit configured to display one of the tomographic images while the image processing unit is generating the combined image and then change from display of the one image of the plurality of the tomographic images to display of the combined image on a display unit.

* * * * *